United States Patent [19]

Kubo et al.

[11] Patent Number: 4,508,648
[45] Date of Patent: Apr. 2, 1985

[54] PHOSPHORIC ESTER OF ANTIBIOTIC OA-6129

[75] Inventors: Katsuro Kubo, Fujisawa; Takeo Yoshioka, Ayase; Mitsuyasu Okabe, Fujisawa; Yasuo Fukagawa, Kamakura; Tomoyuki Ishikura, Chigasaki, all of Japan

[73] Assignee: Sanraku-Ocean Co., Ltd., Tokyo, Japan

[21] Appl. No.: 422,378

[22] Filed: Sep. 24, 1982

[30] Foreign Application Priority Data

Oct. 2, 1981 [JP] Japan .................. 56-156133

[51] Int. Cl.³ .................. C07D 487/04; A61K 31/40
[52] U.S. Cl. .................. 260/245.2 T; 260/245.2 R
[58] Field of Search ............. 424/274; 260/245.2 T, 260/245.2 R

[56] References Cited

U.S. PATENT DOCUMENTS 4,235,917  11/1980  Christensen et al. ........ 260/245.2 T
4,426,390   1/1984  Okabe et al. ............... 260/245.2 T
4,451,401   5/1984  Okabe et al. ............... 260/245.2 T Primary Examiner—Nicholas S. Rizzo
Attorney, Agent, or Firm—James J. Ralabate

[57] ABSTRACT

Novel phosphoric ester of antibiotic OA-6129 presented by the formula

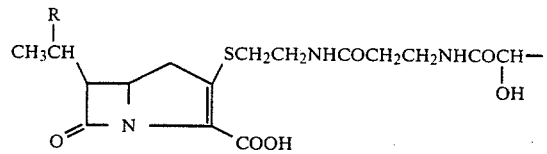

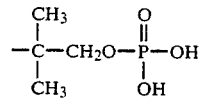

wherein
R is a hydrogen atom, hydroxyl or hydroxysulfonyloxy, and its salts and the preparation method thereof.

1 Claim, No Drawings

PHOSPHORIC ESTER OF ANTIBIOTIC OA-6129

BACKGROUND OF THE INVENTION (1) Field of the Invention

This invention relates to novel phosphoric esters of carbapenem antibiotics presented by the formula

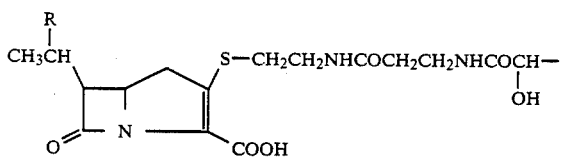

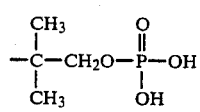

wherein
R is a hydrogen atom, hydroxyl or hydroxysulfonyloxy, and their salts and a preparation method thereof.

(2) Description of the Prior Art

Antibiotic compounds having a generic structure of 7-oxo-1-azabicyclo[3.2.0]hept-2-ene-2-carboxylic acid (carbapenem)

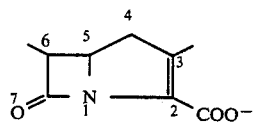

are generally known to have high antimicrobial activity and strong beta-lactamase-inhibitory property. Various types of 7-oxo-1-azabicyclo[3.2.0]hept-2-ene-2-carboxylic derivatives have been prepared by fermentational, semi-synthetic or fully-synthetic methods. Some examples are thienamycin [J. Antibiotics 32, 1-12 (1979)], epithienamycins (Abstracts Nos. 80 and 81, 17th Interscience Conference on Antimicrobial Agents and Chemotherapy), N-acetylthienamycin (German Pat. No. 2652681, 1977), olivanates [J. Antibiotics 32, 287-304 (1979)], PS-5 [J. Antibiotics 32, 262-286 (1979)], PS-6 and PS-7, U.S. Pat. No. 4,368,203.

Some of the present inventors have disclosed in E.P.O. 48,999 that *Streptomyces* sp. OA-6129 produces hitherto-unknown carbapenem compounds designated antibiotics OA-6129A, OA-6129B and OA-6129C presented by the following formula:

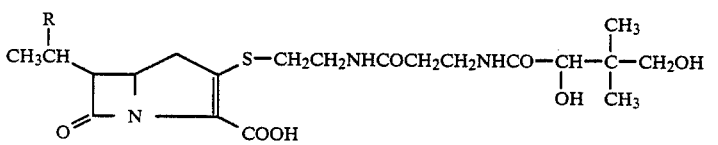

wherein
R is a hydrogen atom, hydroxyl or hydroxysulfonyloxy.

In addition to the fundamental nucleus of 7-oxo-1-azabicyclo[3.2.0]hept-2-ene-2-carboxylate, the new carbapenem compounds have a pantetheinyl group at carbon 3 and an ethyl, 1-hydroxyethyl or 1-hydroxysulfonyloxyethyl group at carbon 6 respectively.

SUMMARY OF THE INVENTION

This invention relates to antibiotic compounds presented by the formula

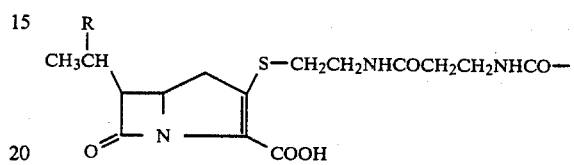

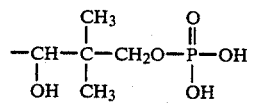

wherein
R is a hydrogen atom, hydroxyl or hydroxysulfonyloxy, and their salts and to a preparation method thereof in which the primary hydroxyl group of carbapenem antibiotics presented by the formula

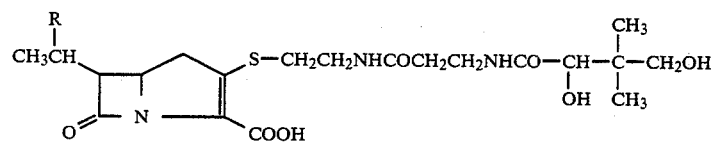

or their salts is enzymatically phosphorylated in the presence of adenosine 5'-triphosphate (ATP) by a microbe having such phosphorylating ability or its processed matter.

DETAILED DESCRIPTION OF THE INVENTION

This invention relates to novel antibiotic compounds. More particularly, it relates to antimicrobial compounds presented by the following formula:

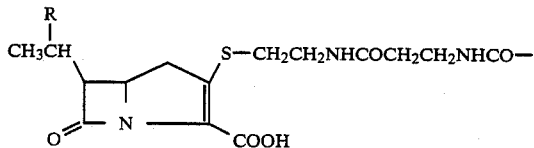

-continued

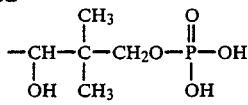

wherein
R is a hydrogen atom, hydroxyl or hydroxysulfonyloxy, and their salts and a preparation method thereof.

The novel antibiotic compounds of this invention presented by formula (I) have a common structural characteristic that the primary hydroxyl group of antibiotics OA-6129A, OA-6129B and OA-6129C (these antibiotics are collectively referred to as antibiotic OA-6129 hereafter) is phosphorylated. If required, the compounds of formula (I) having ethyl (R=H), 1-hydroxyethyl (R=hydroxyl) and 1-hydroxysulfonyloxyethyl

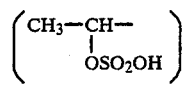

(R=hydroxysulfonyloxy) at carbon 6 are specified as phosphoric esters of antibiotics OA-6129A, OA-6129B and OA-6129C, respectively. These phosphoric esters are collectively called as phosphoric ester of antibiotic OA-6129.

Similar to previously described carbapenem compounds, the novel phosphoric ester of antibiotic OA-6129 presented by formula (I) is useful as an antimicrobial agent, because it has potent antimicrobial activity and strong beta-lactamase-inhibitory property and potentiates synergistically the antibiotic effect of traditional beta-lactam compounds such as penicillins and cephaosporins on beta-lactamase-producing pathogens. It is worth mentioning that the compound of this invention presented by formula (I) is superior in stability to carbapenem compounds described in the literature.

The C-2 carboxyl group and/or the phosphoryl group of the compound of formula (I) may be in the salt form. For example, alkali metals such as sodium, potassium and lithium; alkaline earth metals such as calcium and magnesium; metals such as aluminium; primary, secondary or tertiary amines such as monoethylamine, dimethylamine, trimethylamine, monoethanolamine and diethanaolamine; and organic bases such as benzathine and procaine are employable for preparation of such salts. It is necessary to choose pharmaceutically acceptable salts and thus alkali metal salts such as sodium salt and potassium salt are most favored.

The phosphoric ester of antibiotic OA-6129 presented by formula (I) according to the present invention is produced by treating antibiotic OA-6129A, OA-6129B or OA-6129C (substrate) presented by formula (II), in the presence of adenosine-5'-triphosphate (ATP) under usual enzyme reaction conditions with a microbe or its processed matter having an ability to phosphorylate pantothenic acid in the presence of ATP.

As far as the primary hydroxyl group of antibiotics OA-6129A, OA-6129B and OA-6129C presented by formula (II) can be phosphorylated to give the corresponding products presented by formula (I), the microbe or its processed matter may be selected from a wide variety of species and preparations. In practice, it is advantageous to use a microbe or its processed matter having an ability to phosphorylate pantothenic acid [for example, microbes described in Agricultural and Biological Chemistry, 36, 84–92 (1972)]. One of the favored examples is washed cells of Brevibacterium ammoniagenes ATCC 6871.

The washed cells of Brevibacterium ammoniagenes ATCC 6871 are suspended in a buffered solution in the pH range of 6–8.5 and then allowed to react with antibiotic OA-6129 presented by formula (II) in the presence of ATP as a phosphorylating agent.

The preferred buffer is phosphate solution, the pH of which is adjusted in the range of 6–8.5, favorably 7–8, based on the chemical instability of the compounds presented by formula (II).

The reaction temperature under the said conditions is generally in the range of 20°–45° C., favorably 30°–40° C. The reaction period varies depending on the reaction temperature, the species of the microbe and the type of cellular preparations, but is usually in the length of 30 minutes to 10 hours.

If required, the phosphorylation reaction may be accelerated by addition of a surface-active agent such as sodium higher aliphatic alkylsulfate and/or metal ions such as magnesium.

In practice, it is easy for those skilled in the art to choose optimum reaction conditions for the particular microbe or its processed matter by preliminary small-scale experiments.

The products of this invention presented by formula (I) can be recovered from filtrates, supernatants or extracts by a suitable combination of isolation methods known per se such as filtration, centrifugation, extraction and chromatography.

More particularly, it is advantageous to use various isolation methods known per se for recovery of carboxylic antibiotic compounds. For example, extraction at a low pH with an organic solvent such as ethyl acetate and n-butanol followed by back-transfer into an aqueous solution at a high pH; adsorption on activated carbon, Amberlite XAD (Rohm and Haas Co.) or Diaion HP-20 (Mitsubishi Chemical Industries Ltd.) followed by elution with aqueous methanol or acetone; ion exchange resin column chromatography on Dowex 1×2 (Dow Chemical Co.), QAE-Sephadex A-25 (Pharmacia Fine Chemicals AB), DEAE-cellulose Whatman DE-32 (Whatman Inc.) or DEAE-Sephadex A-25 (Pharmacia Fine Chemicals AB); gel filtration on Sephadex G-10 (Pharmacia Fine Chemicals AB) or Bio-Gel P-2 (Bio-Rad Laboratories); column chromatography on cellulose or Avi-cel SF (American Viscose Corp.); forced precipitation with acetone or other organic solvents; and freeze-drying are used singly or in combination for isolation and purification of the product antibiotics of this invention. If necessary, the same procedure may be repeatedly employed.

The compounds of this invention presented by formula (I) can be quantitatively analyzed during isolation and purification works by bioassay and/or bioautography as detailed later. Thus the phosphoric esters of antibiotics OA-6129A, OA-6129B and OA-6129C are obtained as pure preparations having physico-chemical properties as specified later.

As the phosphoric ester of antibiotic OA-6129 is generally more stable in salt form than in free form, it is advantageous to use the ester in salt form for chemotherapy, chemical derivation and purification.

The phosphoric ester of antibiotic OA-6129 can be transformed into salt form with inorganic and organic bases by various methods known per se. Examples of such inorganic and organic bases are alkali metal hydroxides such as sodium hydroxide, potassium hydroxide and lithium hydroxide; alkaline earth metal hydroxides such as calcium hydroxide and magnesium hydroxide; and primary, secondary or tertiary organic amines such as monomethylamine, dimethylamine, trimethylamine, monoethanolamine, diethanolamine, benzathine and procaine.

The phosphoric ester of antibiotic OA-6129 or its salts according to this invention has a broad spectrum of potent antimicrobial activity against pathogens covering Gram-positive bacteria such as Staphylococcus, Sarcina and Bacillus and Gram-negative bacteria such as Alcaligenes and Comamonas. In addition, the phosphoric ester of antibiotic OA-6129 according to this invention shows a relatively strong antimicrobial potency against Gram-negative pathogens such as Escherichia, Klebsiella and Proteus.

It is worth mentioning that, compared with the parent compound presented by formula (II), the phosphoric ester of antibiotic OA-6129 presented by formula (I) has improved antimicrobial activities against some beta-lactam-resistant Gram-negative bacteria such as Citrobacter, Proteus, Enterobacter, Klebsiella and Serratia; and that it is significantly more stable in kidney homogenates of various mammals.

The antimicrobial spectrum of the phosphoric ester of antibiotic OA-6129 according to this invention is demonstrated in Table 1 by determining the minimum inhibitory concentrations of the compound against various pathogenic microbes.

TABLE 1

Minimum Inhibitory Concentration (M.I.C. in μg/ml)** of the Phosphoric Ester of Antibiotic OA-6129 against Various Microorganisms

| Microorganism | Phosphoric ester of antibiotic OA-6129A | Phosphoric ester of antibiotic OA-6129B | Antibiotic OA-6129A | Cefazolin |
|---|---|---|---|---|
| Bacillus subtilis ATCC 6633 | 3.13 | 25 | 0.39 | 0.10 |
| Sarcina lutea | 6.25 | >25 | 6.25 | 0.39 |
| Staphylococcus aureus 209P | 1.56 | 12.5 | 0.78 | 0.05 |
| Staphylococcus aureus Smith | 3.13 | >25 | 1.56 | 0.20 |
| Staphylococcus aureus Russell | 6.25 | >25 | 0.78 | 0.20 |
| Staphylococcus epidermidis | 6.25 | >25 | 1.56 | 0.20 |
| Alcaligenes faecalis A1 | 1.56 | 6.25 | 1.56 | 3.13 |
| Citrobacter freundii GN346* | >25 | >25 | 50 | >400 |
| Comamonas terrigena B-996 | 0.05 | 0.39 | 0.05 | 0.10 |
| Enterobacter aerogenes E-19* | 12.5 | 25 | 25 | >400 |
| Enterobacter cloacae 45* | 25 | >25 | 50 | >400 |
| Enterobacter sp. E-8 | 3.13 | 12.5 | 12.5 | 1.56 |
| Escherichia coli K-12 | 3.13 | 12.5 | 12.5 | 1.56 |
| Escherichia coli RGN823* | 3.13 | 12.5 | 12.5 | 1.56 |
| Klebsiella pneumoniae K13* | 25 | 12.5 | 50 | 12.5 |
| Proteus mirabilis P-6 | 25 | 25 | 50 | 6.25 |
| Proteus rettgeri P-6 | 12.5 | 12.5 | 25 | 3.13 |
| Proteus vulgaris GN76* | 25 | 25 | 100 | >400 |
| Proteus sp. P-22* | 25 | 25 | 100 | >400 |
| Providencia sp. P-8 | 6.25 | 6.25 | 12.5 | 0.78 |
| Pseudomonas aeruginosa IFO 3445* | >25 | >25 | >100 | >400 |
| Pseudomonas aeruginosa NCTC 10490* | >25 | >25 | >100 | >400 |
| Serratia marcescens S-18* | 25 | 12.5 | 100 | >400 |
| Serratia marcescens T55* | >25 | 25 | 100 | >400 |

*Beta-lactam-resistant strain.
**Medium heart-infusion agar (Difco Lab.); inoculum size $10^6$ cells/ml; determined by the agar dilution technique As described above, the phosphoric ester of antibiotic OA-6129 of this invention is more stable than carbapenem compounds reported in the literature. More particularly, it is obvious from Table 2 that the compound of this invention has a significantly improved stability in kidney homogenates of mammalian animals.

TABLE 2

Relative Stability of the Phosphoric Ester of Antibiotic OA-6129 and Related Carbapenems in Kidney Homogenates of Mouse, Dog and Man*

| Kidney homogenate of | Antibiotic PS-5 | Antibiotic OA-6129A | Phosphoric ester of antibiotic OA-6129A | Antibiotic OA-6129B | Phosphoric ester of antibiotic OA-6129B |
|---|---|---|---|---|---|
| Phosphate buffer, pH 7.0 (control) | 100 | 100 | 114 | 98 | 100 |
| Mouse | 10 | 7 | 47 | 20 | 42 |
| Dog | 10 | 25 | 18 | 20 | 29 |

TABLE 2-continued

Relative Stability of the Phosphoric Ester of Antibiotic OA-6129 and Related Carbapenems in Kidney Homogenates of Mouse, Dog and Man*

| Kidney homogenate of | Antibiotic PS-5 | Antibiotic OA-6129A | Phosphoric ester of antibiotic OA-6129A | Antibiotic OA-6129B | Phosphoric ester of antibiotic OA-6129B |
| --- | --- | --- | --- | --- | --- |
| Man | 28 | 57 | 96 | 47 | 72 |

*A drug solution (100–300 μg/ml) (0.1 ml) and a kidney homogenate (0.1 ml) were allowed to react at 37° C. for 60 minutes and the mixture was immediately heat-treated at 100° C. for 15 seconds. After centrifugation, the concentration of the drug remaining in the supernatant solution was bioassayed as a percentage of initial concentration by *Comamonas terrigena* B-996.

The examples which follow will illustrate the present invention. In the following examples, the phosphoric ester of antibiotic OA-6129 and related carbapenem compounds were qualitatively and quantitatively assayed as explained below.

(1) Bioassay

An overnight culture of *Comamonas terrigena* B-996 on a nutrient agar slant was suspended in nutrient broth to give a cell suspension of absorbance 0.04 at 610 nm. One percent of the cell suspension in volume was inoculated into molten agar medium containing 0.8% in weight of Kyokuto powdered bouillon (Kyokuto Pharmaceutical Co.) and 1.0% in weight of Bato-agar (Difco Lab.), and 7 ml each of the inoculated agar medium was poured into a 9 cm petri dish to make a Comamonas assay plate.

(2) Bioautography

One hundred milliliters of the inoculated molten agar medium was poured into a 32×24 cm rectangular tray instead of a 9 cm petri dish, resulting in a largesize assay plate which could accomodate a paper chromatogram or electrophoretogram or a thin layer chromatogram.

A paper chromatogram containing antibiotic compounds was kept in contact with the agar surface of the assay plate for 15 minutes. After the chromatogram was removed from the agar surface, the large-size assay plate was incubated at 35° C. for 20 hours. Rf values of the antibiotic compounds were calculated from the corresponding positions of halos on the bioautogram (qualitative assay), while the amounts of the antibiotics were roughly estimated based on the sizes of halos (semi-quantitative assay).

In the case of a thin layer chromatogram, a sheet of very thin paper such as tissue paper was intercalated between the chromatogram and the agar surface, before the antibiotic compounds were transferred from the chromatogram into the assay agar medium. After 15 minutes of contact, the chromatogram was removed from the agar surface and the large-size assay tray was incubated at 35° C. for 20 hours for qualitative and semiquantitative assays.

EXAMPLE 1

Cultivation of *Brevibacterium ammoniagenes* ATCC 6871.

One hundred milliliters each of liquid medium composed of 1.0% glucose, 1.5% peptone, 0.3% $K_2HPO_4$, 0.2% NaCl, 0.02% $MgSO_4.7H_2O$ and 0.1% yeast extract (pH 7.0 prior to autoclaving) was distributed into fifty 500-ml Erlenmeyer flasks and autoclaved at 120° C. for 15 minutes. After cooling, the flasks were inoculated aseptically with *Brevibacterium ammoniagenes* ATCC 6871 and shake-cultured at 28° C. for 2 days. The cells were collected by centrifugation, washed twice in 0.01M phosphate buffer, pH 7.1, and suspended in 100 ml of the same buffer. The cell suspension was stored frozen until use.

EXAMPLE 2

Preparation of Phosphoric Ester of Antibiotic OA-6129A

ATP.2Na (300 mg) and $MgSO_4.7H_2O$ (148 mg) were dissolved in 5 ml of distilled water and adjusted to pH 7 with sodium bicarbonate. The ATP-$MgSO_4$ solution, 5 ml of 1M phosphate buffer, pH 7.4, 100 ml of the cell suspension prepared in Example 1 and 100 mg of sodium laurylsulfate were mixed thoroughly. Forty milligrams of antibiotic OA-6129A (sodium salt) was added to the mixture and was kept gently stirred for 4 hours at 35° C. After the cells were removed by centrifugation, an aliquot volume of the supernatant solution was analyzed by high voltage paper electrophoresis (Whatman No. 1 filter paper; 1,500 V/30 cm for 50 minutes in Veronal buffer, pH 8.6). A new antibiotic spot corresponding to the phosphoric ester of antibiotic OA-6129A was located at 11 cm toward the anode on the bioautogram, while the starting material (antibiotic OA-6129A) appeared as a small spot at 4 cm toward the anode.

The supernatant solution was adsorbed on a QAE-Sephadex A-25 column (Pharmacia Fine Chemicals AB; 3.0×40 cm) which had been equilibrated with 0.01M phosphate buffer, pH 7.4. After washing with a small volume of the same buffer, the column was eluted with a linear concentration gradient of sodium chloride in the same buffer. The phosphoric ester of antibiotic OA-6129A was collected at 0.25M sodium chloride. Antimicrobially active fractions containing the phosphoric ester of antibiotic OA-6129A were combined and adsorbed on a chromatographic column of Diaion HP-20AG Mitsubishi Chemical Industries Ltd.; 3.0×40 cm) previously equilibrated with 0.01M phosphate buffer, pH 7.4. By eluting with distilled water, antibiotic fractions were collected and freeze-dried to provide 16 mg of a partially-purified preparation of the phosphoric ester of antibiotic OA-6129A. The partially-purified preparation was dissolved in 1 ml of distilled water and subjected to gel filtration on Cellulofine GC-15-m (Chisso Corp.; 1.9×65 cm). Pure phosphoric ester of antibiotic OA-6129A (12.9 mg) was recovered by freeze-drying.

This preparation of the phosphoric ester of antibiotic OA-6129A possessed the following physical and chemical properties:

(1) U.V. absorption spectrometry in 0.01M phosphate buffer, pH 7.4.

$\lambda_{max}: 302 \text{nm}(E_1 \ _{cm}^{1\%} 87.9)$ (2) Proton N.M.R. spectrometry in D$_2$O (internal standard: DSS)

| δ (ppm) | |
|---|---|
| 0.89 | (3H, s, CH$_3$—$\underline{\text{C}}$—) where CH$_3$ on C |
| 0.97 | (3H, s, CH$_3$—$\underline{\text{C}}$—) where CH$_3$ on C |
| 0.98 | (3H, t, J=7.0 Hz, CH$_2$—$\underline{\text{CH}_3}$) |
| 1.50~2.00 | (2H, m, $\underline{\text{CH}_2}$—CH$_3$) |
| 2.47 | (2H, t, J=6.5 Hz, NH—CH$_2$—$\underline{\text{CH}_2}$—CO) |
| 2.70~3.83 | (11H, m, C—4H$_2$, C—6H, S—$\underline{\text{CH}_2}$—$\underline{\text{CH}_2}$—NH, NH—$\underline{\text{CH}_2}$—CH$_2$—CO, —$\overset{\|}{\text{C}}$—$\underline{\text{CH}_2}$—O—$\overset{\overset{\text{O}}{\|}}{\underset{\underset{\text{ONa}}{\|}}{\text{P}}}$—ONa) |
| 3.85~4.20 | (2H, m, C—5H, HO—$\underline{\text{CH}}$—CO) |

(3) Color reactions
 Positive: Ehrlich, iodoplatinate and molybdate reagents.
 Negative: ninhydrin reagent.
(4) Paper chromatographic data
 Filter paper: Toyo filter paper No. 50.
 Solvent system: acetonitrile/0.1M Tris-HCl buffer, pH 7.5/0.1M ethylene-diaminetetraacetate, pH 7.5=120/30/1.
 Detection: bioautography with *Comamonas terrigena* B-996.
 Rf value: 0.03 (antibiotic OA-6129A: 0.26, antibiotic PS-5: 0.31).
(5) High voltage paper electrophoretic data
 Filter paper: Whatman No. 1.
 Electrophoresis: 1,500 V/30 cm for 50 minutes in Veronal buffer, pH 8.6.
 Detection: bioautography with *Comamonas terrigena* B-996.
 Mobility: 11–12 cm toward the anode (antibiotic OA-6129A: 4–5 cm), antibiotic PS-5: 6–7 cm).
(6) Hydrolysis by phosphatase
 Alkaline phosphatase (Sigma Chemical Co.; P3877) hydrolyzed the phosphoric ester of antibiotic OA-6129A to give antibiotic OA-6129A and phosphate.

EXAMPLE 3

Preparation and Purification of Phosphoric Ester of Antibiotic OA-6129B

By the same procedure as detailed in Example 2, 40 mg of antibiotic OA-6129B was phosphorylated. Solid matters were separated by centrifugation and the supernatant solution was applied on a column (3.0×40 cm) of QAE-Sephadex A-25 (Pharmacia Fine Chemicals AB) which had preliminarily been bufferized with 0.01M phosphate, pH 7.4. The column was washed with the same buffer and then subjected to elution with a linear concentration gradient of sodium chloride in the same buffer. Active fractions containing the phosphoric ester of antibiotic OA-6129B which came out from the column at 0.35M sodium chloride were combined and adsorbed on a Diaion HP-20AG column (Mitsubishi Chemical Industries Ltd.; 3.0×40 cm) previously equilibrated with the phosphate buffer. After the column was washed with the same buffer, the phosphoric ester of antibiotic OA-6129B was eluted with 10% aqueous acetone. Active fractions were united and concentrated to about 1 ml under reduced pressure with a dry-ice trap. Gel filtration with a Cellulofine GC-15-m column (Chisso Corp.; 1.9×65 cm) followed by lyophilization yielded 11.3 mg of the phosphoric ester of antibiotic OA-6129B.

The present preparation of the phosphoric ester of antibiotic OA-6129B showed the following physical and chemical properties:
(1) U.V. absorption spectrometry in 0.01M phosphate buffer, pH 7.4

$\lambda_{max}: 302 \text{ nm}(E_1 \ _{cm}^{1\%} 82.4)$ (2) Proton N.M.R. spectrometry in D$_2$O (internal standard: DSS)

| δ(ppm) | |
|---|---|
| 0.87 | (3H, s, CH$_3$—$\underline{\text{C}}$—) |
| 0.95 | (3H, s, CH$_3$—$\underline{\text{C}}$—) |
| 1.27 | (3H, d, J=7.0 Hz, CH$_3$—$\underline{\text{CH}}$—) with OH on CH |
| 2.47 | (2H, t, J=6.5 Hz, NH—CH$_2$—$\underline{\text{CH}_2}$—CO) |
| 2.80~4.50 | (14H, m, C—4H$_2$, C—5H, C—6H, CH$_3$—$\underline{\text{CH}}$—(OH), S—$\underline{\text{CH}_2}$—$\underline{\text{CH}_2}$—NH, NH—$\underline{\text{CH}_2}$—CH$_2$—CO, —$\overset{\|}{\text{C}}$—$\underline{\text{CH}_2}$—O—$\overset{\overset{\text{O}}{\|}}{\underset{\underset{\text{ONa}}{\|}}{\text{P}}}$—ONa, HO—$\underline{\text{CH}}$—CO) |

(3) Color reactions
 Positive: Ehrlich, iodoplatinate and molybdate reagents.
 Negative: ninhydrin reagent.
(4) Paper chromatographic data
 Filter paper: Toyo filter paper No. 50.
 Solvent system: acetonitrile/0.1M Tris-HCl buffer, pH 7.5/0.1M ethylenediaminetetraacetate, pH 7.5=120/30/1.
 Detection: bioautography with *Comamonas terrigena* B-996.
 Rf value: 0.01 (antibiotic OA-6129A: 0.26, antibiotic PS-5: 0.31).
(5) High voltage paper electrophoretic data Filter paper: Whatman No. 1.
Electrophoresis: 1,500 V/30 cm for 50 minutes in Veronal buffer, pH 8.6.
Detection: bioautography with *Comamonas terrigena* B-996.
Mobility: 11–12 cm toward the anode (antibiotic OA-6129A: 4–5 cm, antibiotic PS-5: 6–7 cm).

(6) Hydrolysis by phosphatase

Alkaline phosphatase (Sigma Chemical Co.; P3877) hydrolyzed the phosphoric ester of antibiotic OA-6129B to give antibiotic OA-6129B and phosphate.

EXAMPLE 4

Preparation of Phosphoric Ester of Antitiotic OA-6129C

One milligram (activity equivalent) of antibiotic OA-6129C was dissolved in 0.2 ml of 0.2M phosphate buffer, pH 7.4, and mixed with 0.05 ml of 100 mM ATP solution (adjusted to pH 6–7 with sodium bicarbonate) and 0.05 ml of 100 mM magnesium sulfate solution. After 0.2 ml of the *Brevibacterium ammoniagenes* cell suspension obtained in Example 1 and 0.5 mg of sodium lauryl-sulfate were added, the reaction mixture was incubated at 35° C. for 4 hours under shaking. The supernatant solution recovered by centrifugation was analyzed by high voltage paper electrophoresis under the below-specified conditions. A halo corresponding to the phosphoric ester of antibiotic OA-6129C was located at 9.4 cm toward the anode, together with a very small spot of the strating material (antibiotic OA-6129C) at 6.5 cm toward the anode.

Conditions for high voltage paper electrophoresis:
Filter paper: Whatman No. 1
Electrophoresis: 1,500 V/30 cm for 30 minutes in Veronal buffer, pH 8.6
Detection: bioautography with *Comamonas terrigena* B-996
Mobility toward the anode: 9–10 cm (antibiotic OA-6129C: 6–7 cm, antibiotic OA-6129A: 2–3 cm, antibiotic PS-5: 4–5 cm).

The electrophoretic area corresponding to the phosphoric ester of antibiotic OA-6129C was cut out and dipped in a small volume of 0.01M phosphate buffer, pH 8.4. The aqueous extract was treated with the alkaline phosphatase, and the reproduction of antibiotic OA-6129C was confirmed by high voltage paper electrophoresis.

For reference, methods for production of antibiotic OA-6129 which is used as the starting material in this invention are described in the following:

(Reference)

(A) Two 500-ml Erlenmeyer flask containing 100 ml each of seed medium S-1 (see below) were sterilized at 120° C. for 15 minutes under usual conditions. One loopful each of mature spores of Streptomyces sp. OA-6129 was inoculated into the flasks and shake-cultured at 28° C. for 48 hours on a rotary shaker (200 rpm; 7 cm throw). The seed culture (200 ml in total) was transferred into a 30-liter jar fermentor containing 15 liters of seed medium SE-4 (see below) and propagated at 28° C. and 400 rpm for 24 hours under forced aeration of 7.5 liter/minute. For anti-foaming, 0.07% in volume of Silicone KM-75 (Shinetsu Chemical Co.) was supplemented.

(B) Two liters of the 24 hour-old seed culture from (A) was inoculated into a 200-liter fermentation tank containing 100 liters of production medium GM-1 (see below). The fermentation was carried out at 28° C. for 90 hours, using an agitation speed of 200 rpm and an aeration rate of 50 liter/minute. For prevention of possible foaming, Silicone KM-75 was added at 0.07%.

The time course of antibiotic OA-6129 production was traced by bioassay using antibiotic PS-5 sodium salt as the standard and is summarized below.

| | Antibiotic titer (as antibiotic PS-5 sodium salt) |
|---|---|
| Period of fermentation | |
| 48 hours | 2.6 μg/ml |
| 72 | 11.5 |
| 90 | 24.0 |
| Seed medium S-1 | |
| Soybean meal | 1.5% (weight/volume) |
| Yeast extract | 0.5% |
| Potato starch | 2.0% |
| CaCO$_3$ | 0.2% |
| pH prior to sterilization | 7.0 |
| Seed medium SE-4 | |
| Beef extract | 0.3% (weight/volume) |
| Tryptone | 0.5% |
| Glucose | 0.1% |
| Soluble starch | 2.4% |
| Yeast extract | 0.5% |
| CaCO$_3$ | 0.4% |
| Soybean meal | 0.5% |
| pH prior to sterilization | 7.5 |
| Production medium GM-1 | |
| Glycerin | 8.0% (weight/volume) |
| Fish meal | 1.0% |
| Soybean meal | 3.0% |
| CaCO$_3$ | 0.3% |
| K$_2$HPO$_4$ | 0.2% |
| MgSO$_4$ | 0.2% |
| pH prior to sterilization | adjusted to 7.2 with NaOH |

Vitamin B$_{12}$ solution in 0.01 M phosphate buffer, pH 5.5, which was separately auto-claved for 5 minutes at 1 KG/cm$^2$.G was supplemented at a final concentration of 0.0005% (weight/volume) before inoculation.

(C) One hundred liters of the 90 hour-old fermentation broth from (B) was mixed with 5% (weight/volume) of Topco Perlite No. 34 (Toko Perlite Co.) and the solids were separated with a basket-type centrifuge, giving 90 liters of the broth filtrate. The filtrate was charged on a column (15×100 cm) of Diaion HP-20 (Mitsubishi Chemical Industries Ltd.). The column was washed with 5 liters of distilled water and eluted with 30% (in volume) aqueous acetone. The eluate was collected in 1.0-liter fractions. Antimicrobially active fractions Nos. 8 through 15 (8.0 liters in total) were combined and adsorbed on a Diaion PA306S column (Mitsubishi Chemical Industries Ltd.: 8×60 cm). After rinsing with 1.0 liter of distilled water, the column was subjected to elution with 3.0% sodium chloride solution. Ten 500-ml fractions from Nos. 7 to 16 (5.0 liters in total) were found to include antibiotics OA-6129A and OA-6129B.

Subsequently the concentration of sodium chloride in the eluent was raised to 30% for elution of antibiotic OA-6129C from the Diaion PA306S column. Antimicrobially active 500-ml fractions from Nos. 3 to 16 (7.0 liters in total) were revealed to contain antibiotic OA-6129C.

Three hundred grams of sodium chloride was added to the 5.0 liter eluate containing antibiotics OA-6129A and OA-5129B, and the solution was applied on a column of Diaion HP-20 (6×150 cm). For desalting, the column was washed with 500 ml of distilled water.

Antibiotic activities were eluted from the column by increasing linearly the concentration of acetone from 0% to 40% in a total volume of 4.0 liters of the acetone-water mixture.

The eluate was fractionated in 17 ml volumes. Antimicrobially active fractions from Nos. 20 to 130 (about 1.8 liters in total) contained antibiotic OA-6129B together with a relatively small amount of antibiotic OA-6129A. Antibiotic OA-6129A was found in about 700 ml of the eluate from fraction Nos. 131 to 170.

Each eluate was lyophilized to give a brown powder.

(D) Purification of Antibiotic OA-6129A: The brown lyophilized powder of antibiotic OA-6129A from (C) was dissolved in a small volume of distilled water and passed through a column of Bio-Gel P-2 (Bio-Rad Laboratories) (8×100 cm). The aqueous eluate was fractionated in 1.0 liter volumes. Antibiotic fractions were collected, combined, and charged on a QAE-Sephadex column (Pharmacia Fine Chemicals AB; 4×40 cm) which had been bufferized with 0.01M phosphate, pH 8.4. After 200 ml of the same buffer was flown, the concentration of sodium chloride was raised linearly from 0% to 4% in a total volume of 3.0 liters of the eluent. All 15-ml fractions were subjected to bioassay for location of the antibiotic activity. Fraction Nos. from 51 to 70 (300 ml in total) contained antibiotic OA-6129A. A yellowish brown powder was obtained by freeze-drying.

The yellowish brown powder was dissolved in a small amount of distilled water and mixed with 5 grams of sodium chloride. The solution was charged on a column (2×50 cm) of Diaion HP-20AG (Mitsubishi Chemical Industries Ltd.) and the column was rinsed first with 50 ml of 5% sodium chloride solution and subsequently with 100 ml of distilled water. Antibiotic activity was eluted with a linear concentration gradient of acetone from 0% to 30% in a total volume of 1.0 liter of the eluent. The volume of each fraction was 10 ml. Antimicrobially active fractions from Nos. 35 to 45 (110 ml in total) were combined and freeze-dried to provide 52 mg of a yellowish brown crude powder of antibiotic OA-6129A.

This powder was dissolved in a minimum volume of distilled water and passed through a column (2×80 cm) of Sephadex G-10 (Pharmacia Fine Chemicals AB). The column was developed with distilled water and the eluate was fractionated in 10 ml volumes. Antimicrobial fractions (30 ml in total) were adsorbed on a chromatographic column (2×30 cm) of QAE-Sephadex A-25 that had preliminarily been equilibrated with 0.01M phosphate buffer, pH 8.4. After rinsing with 50 ml of the same phosphate buffer, the column was eluted with a linearly increasing concentration gradient of sodium chloride from 0% to 5% in a total volume of 800 ml of the eluent. The eluate was divided in 5 ml fractions. By bioassay, 25 ml of the eluate from fraction Nos. 36 to 40 was collected.

The eluate was mixed with 4 g of sodium chloride and then absorbed on a column (2×40 cm) of Diaion HP-20AG. After washing with 50 ml of distilled water, the column was eluted with a linearly increasing concentration gradient of acetone from 0% to 30% in a total volume of 800 ml of the eluent. The eluate was fractionated in 5 ml volumes. Fraction Nos. 105 to 117 (65 ml in total) were found to be antimicrobially active by bioassay.

Lyophilization of the eluate produced 21 mg of a pale yellow powder of antibiotic OA-6129A.

This lyophilized preparation of antibiotic OA-6129A showed the following physical and chemical properties:

(1) Appearance: pale yellow powder.

(2) Specific rotation: $[\alpha]_D^{24}$: 11.6° (c 1.0, 0.01M phosphate buffer, pH 8.4) [the concentration was calculated from U.V. absorbance at 300 nm ($\epsilon = 5600$)].

(3) Molecular formula: theoretical: $C_{20}H_{30}N_3O_7SNa$ (M.W.=479).

(4) U.V. absorption spectrometry in 0.01M phosphate buffer, pH 8.4: $\alpha$max: 300 nm ($\epsilon = 5600$).

(5) I.R. absorption spectrometry in KBr Major peaks in $cm^{-1}$: 1760 (beta-lactam), 1660 (amide), 1600 (carboxylate).

(6) Proton N.M.R. spectrometry in $D_2O$ (internal standard: DSS):

| δ(ppm) | |
|---|---|
| 0.89 | (3H, s, $CH_3-\underset{\|}{\overset{CH_3}{C}}-$) |
| 0.92 | (3H, s, $CH_3-\underset{\|}{\overset{CH_3}{C}}-$) |
| 1.00 | (3H, t, J=7.5 Hz, $CH_2-CH_3$) |
| 1.60~2.00 | (2H, m, $CH_2-CH_3$) |
| 2.48 | (2H, t, J=6.5 Hz, $N-CH_2-CH_2-CO$) |
| 2.80~3.65 | (11H, m, $C-4H_2$, $C-6H$, $S-CH_2-CH_2-N$, $N-CH_2-CH_2-CO$, $C-CH_2-OH$) |
| 3.95 | (2H, m, $C-5H$, $HO-\underset{\|}{CH}-CO$) |

(E) Purification of Antibiotic OA-6129B: The brown powder containing antibiotic OA-6129B together with a trace amount of antibiotic OA-6129A derived from (C) was dissolved in a small volume of distilled water and then charged on a column (8×100 cm) of Bio-Gel P-2. The column was developed with distilled water and 1.0 liter of the eluate was collected on the basis of bioassay results. The eluate was adsorbed on a QAE-Sephadex A-25 column (4×40 cm) previously equilibrated with 0.01M phosphate buffer, pH 8.4. After washing with 200 ml of the same buffer, the column was subjected to desorption with a linearly increasing concentration gradient of sodium chloride from 0% to 4% in the same buffer (total amount of the eluent 3.0 liters). All 15-ml fractions were bioassayed for antibiotic activity and fraction Nos. 51 to 70 were combined to make 300 ml of the active eluate. By freeze-drying, a yellowish brown powder containing antibiotic OA-6129B was obtained.

This powder was dissolved in a small volume of distilled water and mixed with 5 g of sodium chloride. The mixture was adsorbed on a Diaion HP-20AG column (2×50 cm) and the column was rinsed first with 50 ml of 5% sodium chloride solution and then with 100 ml of distilled water. Elution was done by increasing linearly the concentration of acetone from 0% to 30% in water (total eluent 1.0 liter), each fraction being 10 ml. Based on the bioassay results, fraction Nos. 15 to 35 were combined (210 ml in total). A yellowish brown powder of antibiotic OA-6129B was recovered by lyophilization.

The lyophilized preparation of antibiotic OA-6129B had the following physico-chemical characteristics:

(1) Appearance: yellowish brown powder.
(2) Specific rotation: $[\alpha]_D^{24}$: 14.7° (c 1.0, 0.01M phosphate buffer, pH 8.4) [the concentration was calculated from U.V. absorbance at 300 nm ($\epsilon$=5400)].
(3) Molecular formula: theoretical: $C_{20}H_{30}N_3O_8SNa$ (M.W.=495).
(4) U.V. absorption spectrometry in 0.01M phosphate buffer, pH 8.4: λmax: 300 nm ($\epsilon$=5400).
(5) I.R. absorption spectrometry in KBr: Major peaks in cm$^{-1}$: 1760 (beta-lactam), 1660 (amide), 1600 (carboxylate).
(6) Proton N.M.R. spectrometry in $D_2O$ (internal standard: DSS):

δ(ppm)

0.87    (3H, s, $CH_3$—$\underline{C}$—), $CH_3$ 0.92    (3H, s, $CH_3$—$\underline{C}$—), $\underline{CH_3}$ 1.28    (3H, d, J=7.0 Hz, $CH_3$—$\underline{CH}$—), OH 2.45    (2H, t, J=7.0 Hz, NH—$CH_2$—$\underline{CH_2}$—CO)

3.94    (1H, s, HO—$\underline{CH}$—CO)

(F) Purification of Antibiotic OA-6129C: The eluate (7.0 liters) containing antibiotic OA-6129C derived from (C) was adsorbed on a Diaion HP-20 column (5×80 cm) and the column was washed with 1.5 liters of 0.01M phosphate buffer, pH 8.4. Antibiotic OA-6129C was desorbed from the column by linearly raising the acetone concentration from 0% to 20% in water (total volume of the eluent was 6.0 liters). The eluate was fractionated in 250 ml volumes and fraction Nos. 9 to 13 were united to give 1.25 liters of the eluate.

The eluate was extracted with 1.0 liter of methylene chloride containing 3% alkyldimethylbenzylammonium chloride (Tokyo Chemical Co.). The methylene chloride extract was back-extracted with 300 ml of 8% aqueous sodium iodide. The aqueous extract (300 ml) was charged on a column (8×100 cm) of Bio-Gel P-2 which had previously been bufferized with 0.01M phosphate buffer, pH 8.4. The column was developed with the same buffer and 1.2 liters of the antimicrobially active eluate was collected by bioassay.

The eluate was applied on a Diaion HP-20 column (4×60 cm). The column was washed with 600 ml of distilled water and then eluted with 3.0 liters of aqueous acetone in which the acetone concentration linearly rose from 0% to 10%. The fraction volume was 15 ml. Fraction Nos. 41 to 115 (1.1 liters in total) were found to contain the antibiotic by bioassay. The combined fractions were adsorbed on a QAE-Sephadex A-25 column (4×40 cm) equilibrated with 0.01M phosphate buffer, pH 8.4, beforehand, and the column was washed with 500 ml of the same phosphate buffer. Antibiotic OA-6129C was desorbed with a linearly increasing concentration gradient of sodium chloride from 0% to 5% in a total volume of 3.0 liters of the eluent. The eluate was fractionated in 15 ml volumes. Antimicrobially active fractions from Nos. 112 to 139 were combined to make 420 ml of the eluate. Sodium chloride was added to the eluate at a final concentration of 5% and the solution was charged on a Diaion HP-20AG column (3×60 cm). The column was developed with distilled water and 15 ml each of the eluate was collected on a fraction collector. Two hundred seventy milliliters of the antimicrobially active eluate was obtained from fraction Nos. 31 to 48. Lyophilization of the solution resulted in 135 mg of a yellowish brown powder.

This powder in a small amount of distilled water was placed on a Sephadex G-10 column (2×70 cm) and developed with distilled water. Active eluate (68 ml in total) was collected under antimicrobial monitoring by bioassay.

The eluate was adsorbed on a column (4×30 cm) of QAE-Sephadex A-25 bufferized previously with 0.01M phosphate buffer, pH 8.4. The column was washed with 800 ml of the phosphate buffer and then eluted with a linearly increasing concentration gradient of sodium chloride from 0% to 5% in 2.4 liters of the phosphate buffer. All 13-ml fractions were checked for antimicrobial activity and fraction Nos. 118 to 139 were combined to give 286 ml of the active eluate.

Sodium chloride was added to the eluate to reach a final concentration of 5%. The solution was charged on a Diaion HP-20AG column (3×60 cm) and eluted with distilled water. The volume of each fraction was 10 ml. Fractions having a U.V. absorption maximum at 300 nm were combined to make a total volume of 90 ml. Eighteen milligrams of a pale yellow powder of antibiotic OA-6129C was obtained from the eluate by freeze-drying.

The following are the physical and chemical characteristics of the lyophilized preparation of antibiotic OA-6129C:

(1) Appearance: pale yellow powder.
(2) Specific rotation: $[\alpha]_D^{24}$: 17.4° (c 0.55, 0.01M phosphate buffer, pH 8.2).
(3) Elemental analysis: Calculated for $C_{20}H_{29}N_3O_{11}S_2Na_2 \cdot 2H_2O$: C,37.91%, H,5.25%, N,6.63%, S,10.12%. Found: C,37.61%, H,5.00%, N,6.38%, S,9.52%.
(4) Molecular weight: 597.5731 (molecular formula $C_{20}H_{29}N_3O_{11}S_2Na_2$).
(5) U.V. absorption spectrometry in 0.01M phosphate buffer, pH 8.2: λmax: 300.5 nm ($\epsilon$=7600).
(6) I.R. absorption spectrometry in KBr: Major peaks in cm$^{-1}$: 1750 (beta-lactam), 1660–1595 (amide and carboxylate), 1250–1220 (sulfuric ester).
(7) Proton N.M.R. spectrometry in $D_2O$ (internal standard: DSS):

δ(ppm)

0.86    (3H, s, $CH_3$—$\underline{C}$—), $CH_3$ 0.89    (3H, s, $CH_3$—$\underline{C}$—), $\underline{CH_3}$ 1.49    (3H, d, J=6.5 Hz, $CH_3$—CH—)

2.47    (2H, t, J=7.0 Hz, NH—$CH_2$—$\underline{CH_2}$—CO)

2.70~3.10    (10H, m, $\underline{C—4H_2}$, —$\underline{CH_2}$—OH,

| | -continued |
|---|---|
| | NH—CH₂—CH₂—CO, S—CH₂—CH₂—NH) |
| 3.83 | (1H, dd, J=5.5 Hz, J=9.5 Hz, C—6H) |
| 3.94 | 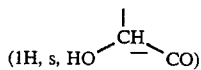 (1H, s, HO—CH—CO) |
| 4.10~4.43 | (1H, m, C—5H) |
| 4.78 | (1H, dd, J=6.5 Hz, J=9.5 Hz, 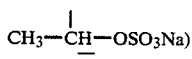 CH₃—CH—OSO₃Na) |
What is claimed is:
1. Compounds presented by the formula
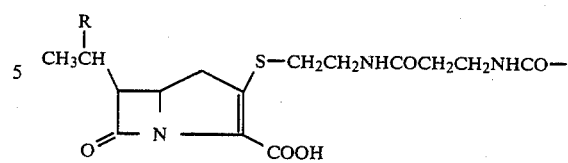 (I)
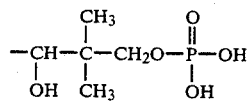
wherein
R is a hydrogen atom, hydroxyl or hydroxysulfonyloxy, and non-toxic pharmaceutically acceptable salts thereof.
* * * * *